United States Patent
Henning

(10) Patent No.: US 6,946,139 B2
(45) Date of Patent: Sep. 20, 2005

(54) METHODS FOR PRODUCING FOAM FROM MULTIPHASE COMPOSITIONS

(75) Inventor: Torsten Henning, Bad Soden (DE)

(73) Assignee: Clariant GmbH, Frankfurt (DE)

( * ) Notice: Subject to any disclaimer, the term of this patent is extended or adjusted under 35 U.S.C. 154(b) by 240 days.

(21) Appl. No.: 10/308,488

(22) Filed: Dec. 3, 2002

(65) Prior Publication Data

US 2004/0105825 A1 Jun. 3, 2004

(51) Int. Cl.$^7$ .............................. A61K 7/00; A61K 7/42
(52) U.S. Cl. .......................... 424/401; 424/59; 424/60; 424/400
(58) Field of Search .......................... 424/59, 60, 400, 424/401

(56) References Cited

U.S. PATENT DOCUMENTS

| | | | |
|---|---|---|---|
| 5,104,645 A | 4/1992 | Cardin et al. | 424/70 |
| 5,635,469 A | 6/1997 | Fowler et al. | 510/406 |

FOREIGN PATENT DOCUMENTS

| | | |
|---|---|---|
| DE | 197 42 480 | 4/1999 |
| DE | 199 55 375 | 6/2001 |
| EP | 0558423 B1 | 5/1996 |
| EP | 1108421 | 6/2001 |
| WO | WO 01/35904 | 5/2001 |

OTHER PUBLICATIONS

English abstract for DE 19955375, Jun. 7, 2001.
K. Shinoda, et al., Emulsions and Solubilidation, Wiley, New York, 1986, pp. 71–82.
English abstract for DE 19742480, Apr. 1, 1999.
English abstract for WO 01/35904, May 25, 2001.

*Primary Examiner*—Shelley A. Dodson
(74) *Attorney, Agent, or Firm*—Richard P. Silverman

(57) ABSTRACT

The invention relates to the use of multiphase compositions comprising
a) at least one oil phase and b) at least one aqueous phase for foaming from foam dispensers. The compositions are preferably cosmetic compositions, particularly preferably sunscreen compositions.

29 Claims, No Drawings

METHODS FOR PRODUCING FOAM FROM MULTIPHASE COMPOSITIONS

DE 199 55 375 describes foamable cosmetic sunscreen compositions in the form of O/W emulsions. To bring about oil phase and aqueous phase, the emulsions comprise emulsifiers. The compositions are foamed from special foam dispensers and can thus be spread on the skin easily and uniformly.

Surprisingly, it has now been found that multiphase compositions comprising oil phases and aqueous phases can be foamed particularly readily from foam dispensers and form an improved foam. For cosmetic applications, the feel on the skin and the spreadability on the skin are significantly improved. Compared with emulsions, the compositions have the advantage that they may be free from emulsifiers, which are sometimes regarded as physiologically unacceptable.

Accordingly, the invention provides the use of multiphase compositions comprising
 a) at least one oil phase and
 b) at least one aqueous phase
for foaming from foam dispensers.

Multiphase compositions are understood as meaning those in which the oil phases and the aqueous phases are each present as macroscopic phases separate from one another. The compositions according to the invention are thus not emulsions, which regularly comprise emulsifiers to bring about the oil phase and aqueous phase.

The compositions are preferably two-phase systems which consist of an oil phase and an aqueous phase.

The proportion of the oil phases, based on the finished compositions, is preferably 1 to 50% by weight, particularly preferably 3 to 40% by weight. The proportion of the aqueous phases, based on the finished compositions, is preferably 50 to 99% by weight, particularly preferably 60 to 97% by weight.

Suitable oil phases are preferably Guerbet alcohols, fatty acid esters, esters of fatty alcohols, triglycerides, vegetable oils, aliphatic and cycloaliphatic hydrocarbons, ethers, silicone oils and/or sunscreen compounds. The oil phase can additionally also comprise perfume oils. As oil phase, particular preference is given to Guerbet alcohols having 6 to 18, preferably 8 to 10, carbon atoms; esters of linear ($C_6$–$C_{13}$)-fatty acids with linear ($C_6$–$C_{20}$)-fatty alcohols; esters of branched ($C_6$–$C_{13}$)-carboxylic acids with linear ($C_6$–$C_{20}$)-fatty alcohols; esters of linear ($C_6$–$C_{18}$)-fatty acids with branched alcohols, preferably 2-ethylhexanol; esters of linear and branched ($C_6$–$C_{13}$)-fatty acids with polyhydric alcohols, preferably dimerdiol and trimerdiol and/or Guerbet alcohols having 6 to 18 carbon atoms;
triglycerides based on ($C_6$–$C_{10}$)-fatty acids; avocado oil; almond oil; olive oil; jojoba oil, dialkyl ethers; hexadecane; cyclohexane; substituted cyclohexanes;
as silicone oils, particular preference is given to cyclomethicone, dimethicone, alkyl methicones, preferably caprylyl methicone, dialkyl methicones, preferably stearyl dimethicone, ($C_{20}$–$C_{24}$)-alkyl dimethicones and/or ($C_{24}$–$C_{28}$)-alkyl dimethicones, caprylyl trimethicone, phenyl trimethicone, dimethylpolysiloxane, methylphenylpolysiloxanes, cyclic silicones, and amino-, fatty acid-, alkyl-, polyether-, epoxy-, fluorine- and/or alkyl-modified silicone compounds, and also polyalkylsiloxanes, polyalkylarylsiloxanes and polyether siloxane copolymers, as described in U.S. Pat. No. 5,104,645 and the specifications cited therein, which may either be in liquid form or else in the form of a resin at room temperature.

As oil phase-forming sunscreen compounds, particular preference is given to 2-ethylhexyl p-methoxycinnamate, ethylhexyl salicylate, octocrylene, oxybenzone/ benzophenone-3, benzophenone-4, benzophenone-5, ethylhexyl N,N-dimethylaminobenzoate, 4-aminobenzoic acid/ PABA, ethylhexyl dimethyl PABA, phenylbenzimidazolesulfonic acid, homomenthyl salicylate, homosalate, isoamyl methoxycinnamate, 4-methylbenzylidenecamphor, 3-benzylidenecamphor, benzene-1,4-[bis(3-methylidenecamphor methylsulfonic] acid), camphor benzalkonium methosulfate, butylmethoxydibenzoylmethane, polyacrylamidomethylbenzylidenecamphor, PEG-25 PABA, ethylhexyltriazone, drometrizole trisiloxane, methylenebisbenztriazolyl tetramethylbutylphenol, dioctylbutamidotriazone, bisethylhexyloxyphenol methoxyphenoltriazines and mixtures thereof.

The aqueous phases are preferably aqueous solutions comprising foam-boosting surfactants, alcohols, salts, polymers and/or further care additives.

In a particularly preferred embodiment, the aqueous phases comprise foam-boosting surfactants which considerably improve the foam formation and the foam quality.

It is essential for the use of the surfactants here that the surfactants are chosen or added in an amount such that the multiphase character of the compositions is retained. I.e. the surfactants must not act like an emulsifier for the respective oil/water system, which would lead to the formation of an emulsion. According to Griffin (K. Shinoda et al., Emulsions and Solubilisation, Wiley, New York, 1986, page 72), it is known that only those surfactants which have an HLB value (hydrophilic lipophilic balance) of less than 18 function as emulsifiers. Accordingly, the foam-boosting surfactants preferably have an HLB value greater than 18, particularly preferably greater than 20, especially preferably from 20 to 40.

Surprisingly, it has been found that anionic surfactants are particularly suitable as foam-boosting surfactants.

As foam-boosting surfactants, particular preference is given to acyl glutamates, ($C_{10}$–$C_{20}$)-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkane sulfates, alkanesulfonates and hydroxyalkanesulfonates, olefin sulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol ether phosphates, protein fatty acid condensation products, alkyl monoglyceride sulfates and sulfonates, alkyl glyceride ether sulfonates, fatty acid methyl taurides, fatty acid sarcosinates, sulforicinoleates, amphoacetates and/or amphoglycinates.

Particularly preferred surfactants are acyl glutamates, preferably sodium lauroyl glutamate and/or sodium cocoylglutamate.

The surfactants are preferably used in the form of their water-soluble or water-dispersible salts, preferably in the form of the sodium, potassium, magnesium, ammonium, mono-, di- and triethanolammonium and analogous alkylammonium salts.

The proportion of the foam-boosting surfactants in the aqueous phases, based on the aqueous phases, is preferably 0.1 to 50% by weight, particularly preferably 0.1 to 20% by weight, especially preferably 0.3 to 15% by weight.

Surprisingly, it has been found that the compositions according to the invention can be foamed particularly advantageously if the oil phases and/or the aqueous phases, particularly preferably the oil phases and the aqueous phases, are present in low-viscosity form.

The viscosities of the oil phases are preferably 1 to 1000 mPas, particularly preferably 10 to 500 mPas.

The viscosities of the aqueous phases are preferably 1 to 1000 mPas, particularly preferably from 10 to 500 mPas.

In addition, it has been found that the addition of 0.01–5% by weight of electrolytes and/or mono- and/or polyhydric alcohols, in each case based on the aqueous phases, has a particularly advantageous effect on the foamability. Suitable electrolytes are preferably salts of alkali metals and/or alkaline earth metals, preferably sodium chloride and/or potassium chloride. Suitable alcohols are preferably propylene glycol, isopropanol, ethanol and/or polyethylene glycols. Preference is given to polyethylene glycols with a relative molecular mass between 200 and 600 g/mol, preferably in amounts of from 0.1 to 45% by weight, based on the aqueous phase.

The compositions are preferably cosmetic compositions, particularly preferably skincare compositions. The skincare compositions can be applied as emulsions. Of particular suitability are the compositions as sunscreen compositions, preferably as sunscreen foams. In the case of sunscreen compositions, it has proven particularly advantageous if the sunscreen compounds present therein themselves form, or at least partially form, the oil phase.

As auxiliaries and additives, the cosmetic compositions may comprise UV protectants, self-tanning agents, thickeners, superfatting agents, carrier materials, silicone compounds, hydrophilic components, fats, waxes, biogenic active ingredients, antioxidants, hydrotropic agents, cationic polymers, glycerol, preservatives, dispersants, protein derivatives, such as gelatin, collagen hydrolysates, pure- and synthetic-based polypeptides, fatty alcohols, deodorizing agents, substances with a keratolytic and keratoplastic action, enzymes and carrier substances, moisture-donating substances, antimicrobially effective agents, dyes and/or fragrances.

Preferred self-tanning agents are dihydroxyacetones.

Suitable superfatting agents are preferably fatty acid alkanolamides, which also serve as foam stabilizers.

Typical examples of fats are glycerides, suitable waxes are, inter alia, beeswax, paraffin waxes or microcrystalline waxes, optionally in combination with hydrophilic waxes, e.g. cetylstearyl alcohol.

Suitable as hydrophilic components are preferably the "soil release polymers", in particular oligo esters, obtained by polycondensation of from 40 to 52 mol %, preferably 45 to 50 mol %, of one or more dicarboxylic acids or esters thereof with 10 to 40 mol %, preferably 20 to 35 mol % of ethylene glycol and/or propylene glycol, 3 to 20 mol %, preferably 10 to 15 mol %, of polyethylene glycol, 0 to 10 mol % of a water-soluble addition product of from 5 to 80 mol of an alkylene oxide onto 1 mol of ($C_1$–$C_{24}$)-alcohols, ($C_6$–$C_{18}$)-alkylphenols or ($C_8$–$C_{24}$)-alkylamines or 0 to 10 mol % of one or more polyols having 3 to 6 hydroxyl groups.

Fungicidal active ingredients which can be used are ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, Zn pyrithione and/or octopirox.

Care substances which can be used are allantoin and bisabolol, preferably in amounts of from 0.0001 to 10% by weight.

Suitable antioxidants are preferably superoxide dismutase, tocopherol (vitamin E) and ascorbic acid (vitamin C) and/or derivatives thereof.

Cationic polymers are preferably cationic cellulose derivatives, cationic starch, copolymers of diallylammonium salts and acrylamides, quaternized vinylpyrrolidone/vinylimidazole polymers, condensation products of polyglycols and amines, quaternized collagen polypeptides, quaternized wheat polypeptides, polyethyleneimines, cationic silicone polymers, such as, for example, amidomethicones, copolymers of adipic acid and dimethylaminohydroxypropyldiethylenetriamine, polyaminopolyamides and/or cationic chitin derivatives, such as, for example, chitosan.

The preparations according to the invention can be mixed with conventional ceramides, pseudoceramides, fatty acid N-alkylpolyhydroxyalkylamides, cholesterol, cholesterol fatty acid esters, fatty acids, triglycerides and/or cerebrosides.

Available moisture-donating substances are preferably glycerol and/or sorbitol, which are preferably used in amounts of from 0.1 to 50% by weight.

The sunscreen compositions can comprise one or more sunscreen compounds, which scatter, reflect or absorb UV radiation. In this connection, the sunscreen compounds can, as already mentioned, also serve simultaneously as the oil phase.

Preferred sunscreen compounds are 2-ethylhexyl p-methoxycinnamate, ethylhexyl salicylate, octocrylene, oxybenzone/benzophenone-3, benzophenone-4, benzophenone-5, ethylhexyl N,N-dimethylaminobenzoate, 4-aminobenzoic acid/PABA, ethylhexyl dimethyl PABA, phenylbenzimidazolesulfonic acid, homomenthyl salicylate, homosalate, isoamyl methoxycinnamate, 4-methylbenzylidenecamphor, 3-benzylidenecamphor, benzene-1,4-[bis(3-methylidenecamphor methylsulfonic acid)], camphor benzalkonium methosulfate, phenylbenzimidazolesulfonic acid terephthalidenedicamphorsulfonic acid, butylmethoxydibenzoylmethane, benzylidenecamphorsulfonic acid, polyacrylamidomethylbenzylidenecamphor, PEG-25 PABA, ethylhexyltriazone, drometrizole trisiloxane, methylenebisbenztriazolyl tetramethylbutylphenol, dioctylbutamidotriazone, disodium phenyldibenzimidazoletetrasulfonate, bisethylhexyloxyphenol methoxyphenoltriazines, 4-isopropylbenzyl salicylate, tetraphthalylidenedicamphordisulfonic acid and mixtures thereof. Pigments/micropigments which can be used are surface-treated or untreated titanium dioxide, iron oxide and/or zinc oxide and mixtures thereof.

The compositions are preferably prepared by mixing together the oil components and the aqueous components, drawing them off and allowing them to separate.

The invention also provides a method of producing foam, which comprises foaming a multiphase composition comprising a) at least one oil phase and b) at least one aqueous phase by means of a foam dispenser.

The invention likewise provides foam dispensers comprising multiphase compositions which comprise a) at least one oil phase and b) at least one aqueous phase.

In the case of the method and the foam dispensers, the compositions are preferably two-phase systems which consist of an oil phase and an aqueous phase. The proportion of the oil phase, based on the finished composition, is preferably 1 to 50% by weight, particularly preferably 3 to 40% by weight. The proportion of the aqueous phase, based on the finished compositions, is preferably 50 to 99% by weight, particularly preferably 60 to 97% by weight. As oil phase, the compounds already described are particularly suitable. Preferably, the aqueous phase comprises at least one of the foam-boosting surfactants already described.

The method of producing foam is not limited to generating cosmetic foams, but is suitable in general for producing foam, including for an industrial scale.

Foam dispensers are understood as meaning all apparatuses which are suitable for the foaming of compositions (mechanic, hydraulic etc.), including those for industrial applications. Preferred foam dispensers are spray containers. Surprisingly, it has been found that the compositions are particularly suitable for spraying from mechanical foam dispensers without a propellant gas (e.g. the products "squeeze foamer" and "F2 finger pump foamer" from Arispray International BV). In order to achieve good foam formation, the oil phases and aqueous phases are preferably mixed together mechanically, preferably by simple shaking, prior to foaming.

The example below serves to illustrate the subject-matter of the invention in more detail without limiting it thereto. The quantities are percentages by weight.

EXAMPLE

Sunscreen Foam

| A | ® Eusolex 2292 (Ethylhexyl Methoxycinnamate) | (Merck) | 8.00% |
|---|---|---|---|
|   | ® Eusolex HMS (Homosalate) | (Merck) | 8.00% |
|   | ® Eusolex 9020 (Butyl Methoxydibenzoylmethane) | (Merck) | 4.00% |
|   | ® Eusolex 6300 (4-Methylbenzylidene Camphor) | (Merck) | 4.00% |
|   | Isopropyl Palmitate |   | 2.00% |
|   | ® SilCare Silicone 41M15 (Caprylyl Methicone) | (Clariant) | 1.00% |
|   | ® Eutanol G (Ethylhexyldodecanol) | (Cognis) | 2.00% |
| B | ® Eusolex 232 (Phenylbenzimidazole Sulfonic Acid) | (Merck) | 4.00% |
|   | Trometamine |   | 2.21% |
|   | Glycerol |   | 7.00% |
|   | Panthenol |   | 0.50% |
|   | ® Hostapon CLG (Sodium Lauroyl Glutamate) | (Clariant) | 1.00% |
|   | Water |   | ad 100% |
|   | Preservative |   | q.s. |
|   | Sodium chloride |   | 1.00% |
| C | Perfume |   | 0.30% |

Preparation:

Phases A, B and C were mixed together and then phase separation into an oil phase and an aqueous phase was awaited.

Foaming:

Foaming took place by means of a F2 finger pump foamer from Airspray International BV.

Here, a spontaneous foam formation was observed, which generated a creamy, fine-pored, readily spreadable, stable foam. The cosmetic composition absorbed well into the skin and left behind a pleasant care feel on the skin.

What is claimed is:

1. A method for dispensing a foam comprising foaming from a foam dispenser a multiphase composition comprising
    a) at least one oil phase and
    b) at least one aqueous phase comprising a foam-boosting surfactant,
wherein said multiphase composition is free of emulsifier.

2. The use as claimed in claim 1, wherein the multiphase composition is a two-phase system.

3. The method of claim 1, wherein the proportion of the oil phases, based on the finished compositions, is 1 to 50% by weight.

4. The method of claim 1, wherein a proportion of the aqueous phase, based on a finished composition, is 50 to 99% by weight.

5. The method of claim 1, wherein the oil phase is selected from the group consisting of Guerbet alcohols, fatty acid esters, esters of fatty alcohols, triglycerides, vegetable oils, aliphatic and cycloaliphatic hydrocarbons, ethers, silicone oils, sunscreen compounds, and mixtures thereof.

6. The method of claim 1, wherein the foam-boosting surfactant has an HLB value greater than 18.

7. The method of claim 6, wherein the foam-boosting surfactant is selected from the group consisting of acyl glutamates, ($C_{10}$–$C_{20}$)-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkens sulfates, alkanesulfonates and hydroxyalkanesulfonates, olefin sulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol ether phosphates, protein fatty acid condensation products, alkyl monoglyceride sulfates and sulfonates, alkyl glyceride ether sulfonates, fatty acid methyl taurides, fatty acid sarcosinates, sulforicinoleates, amphoacetates, amphoglycinates, and mixtures thereof.

8. The method of claim 7, wherein the foam-boosting surfactant comprises acyl glutamates.

9. The method of claim 1, wherein a proportion of the foam-boosting surfactant in the aqueous phase is 0.1 to 50% by weight.

10. The method of claim 1, wherein the viscosities of the oil phase and of the aqueous phase are in each case 1 to 1000 mPas.

11. The method of claim 1, wherein the multiphase composition comprises 0.01 to 5% by weight of electrolytes and/or mono- and/or polyhydric alcohols based on the aqueous phase.

12. The method of claim 12, wherein the electrolytes are alkali metal salts and/or alkaline earth metal salts.

13. The method of claim 12, wherein said alcohols are selected from the group consisting of propylene glycol, isopropanol, ethanol, polyethylene glycols, and mixtures thereof.

14. The method of claim 1, wherein the multiphase composition is a cosmetic composition.

15. The method of claim 15, wherein the cosmetic composition comprises sunscreen compositions.

16. The method of claim 1, wherein the at least one oil phase comprises one or more sunscreen compounds.

17. A method of preparing foam, which comprises foaming a multiphase composition comprising
    a) at least one oil phase and
    b) at least one aqueous phase comprising a foam-boosting surfactant.
with a foam dispenser, wherein said multiphase composition is free of emulsifier.

18. A foam dispenser comprising a pump foamer containing at least one multiphase composition which comprises
    a) at least one oil phase and
    b) at least one aqueous phase comprising a foam-boosting surfactant,
wherein said multiphase composition is free of emulsifier.

19. The method of claim 1, wherein the foam dispenser is a spray container.

20. The method of claim 1, wherein the foam dispenser is a mechanical foam dispenser without propellant gas.

21. The method of claim 1, wherein the proportion of the oil phases, based on the finished compositions, is 3 to 30% by weight.

22. The method of claim 6, wherein the foam-boosting surfactant has an HLB value greater than 20.

23. The method of claim 6, wherein the foam-boosting surfactant has an HLB value from 20 to 40.

24. The method of claim 7, wherein the foam-boosting surfactant comprises sodium lauroyl glutamate and/or sodium cocoyl glutamate.

25. The method of claim 1, wherein a proportion of the foam-boosting surfactant in the aqueous phase is 0.3 to 20% by weight.

26. The method of claim 1, wherein the viscosities of the oil phase and of the aqueous phase are in each case 10 to 500 mPas.

27. The method of claim 1, wherein the multiphase composition is a skincare composition.

28. The method of claim 15, wherein the cosmetic composition comprises a sunscreen foam.

29. A method for producing foam from a multiphase composition, said method comprising
   a) mechanically mixing the multiphase composition having at least two phases and comprising least one oil phase and at least one aqueous phase comprising a foam-boosting surfactant, said multiphase composition being free of emulsifier, to provide a phase mixture;
   b) foaming the phase mixture without a propellant in a foamer to generate the foam.

* * * * *